(12) United States Patent
Overmyer et al.

(10) Patent No.: US 10,478,257 B2
(45) Date of Patent: Nov. 19, 2019

(54) ROBOTIC SURGICAL TOOL, SYSTEM, AND METHOD

(71) Applicant: Ethicon LLC, Guaynabo, PR (US)

(72) Inventors: Mark Overmyer, Cincinnati, OH (US); Jeffrey S. Swayze, Hamilton, OH (US)

(73) Assignee: Ethicon LLC, Guaynabo, PR (US)

( * ) Notice: Subject to any disclaimer, the term of this patent is extended or adjusted under 35 U.S.C. 154(b) by 385 days.

(21) Appl. No.: 15/422,735

(22) Filed: Feb. 2, 2017

(65) Prior Publication Data

US 2018/0214218 A1 Aug. 2, 2018

(51) Int. Cl.
| | |
|---|---|
| *B25J 9/10* | (2006.01) |
| *G01D 5/32* | (2006.01) |
| *A61B 17/00* | (2006.01) |
| *F16H 19/00* | (2006.01) |
| *A61B 34/30* | (2016.01) |
| *B25J 9/16* | (2006.01) |
| *G01D 5/347* | (2006.01) |
| *A61B 34/00* | (2016.01) |
| *A61B 90/00* | (2016.01) |

(52) U.S. Cl.
CPC .............. *A61B 34/30* (2016.02); *A61B 34/76* (2016.02); *B25J 9/104* (2013.01); *B25J 9/1694* (2013.01); *F16H 19/005* (2013.01); *G01D 5/3473* (2013.01); *A61B 2034/303* (2016.02); *A61B 2034/305* (2016.02); *A61B 2090/067* (2016.02); *A61B 2090/0811* (2016.02); *Y10S 901/21* (2013.01)

(58) Field of Classification Search
CPC ... A61B 34/30; A61B 34/76; A61B 2034/303; A61B 2034/305; A61B 2090/067; A61B 2090/0811; B25J 9/104; B25J 9/1694; F16H 19/005; G01D 5/3473; Y10S 901/21
See application file for complete search history.

(56) References Cited

U.S. PATENT DOCUMENTS

| | | | |
|---|---|---|---|
| 5,278,587 A * | 1/1994 | Strauch | G03G 15/0152 347/118 |
| 7,975,568 B2 * | 7/2011 | Zhang | B25J 9/042 74/490.03 |
| 8,114,345 B2 | 2/2012 | Dlugos, Jr. et al. | |

(Continued)

FOREIGN PATENT DOCUMENTS

| | | |
|---|---|---|
| EP | 2364651 A1 | 9/2011 |
| WO | 2014151621 A1 | 9/2014 |

OTHER PUBLICATIONS

International Search Report and Written Opinion for International App. No. PCT/IB2018/050503 dated Apr. 9, 2018 (13 pages).

(Continued)

*Primary Examiner* — Adam D Rogers

(57) ABSTRACT

Methods and devices are provided for robotic surgery, and in particular for measuring a rotational position of elongate shafts of surgical tools. For example, a surgical tool is provided with an elongate shaft having an end effector at a distal end thereof. The elongate shaft is rotatable about a longitudinal axis of the shaft, and the surgical tool is configured to measure a rotational position of the shaft about the longitudinal axis relative to an initial position.

20 Claims, 4 Drawing Sheets

(56) References Cited

U.S. PATENT DOCUMENTS

| | | |
|---|---|---|
| 8,910,537 B2 * | 12/2014 | Nakamura ............. A61B 90/50 |
| | | 74/490.04 |
| 9,474,988 B2 * | 10/2016 | Shatzkin ................. A63J 1/028 |
| 9,492,234 B2 * | 11/2016 | Comber ................. A61B 34/30 |
| 2007/0060879 A1 | 3/2007 | Weitzner et al. |
| 2011/0238010 A1 | 9/2011 | Kirschenman et al. |
| 2013/0123802 A1 | 5/2013 | Comber et al. |
| 2018/0168677 A1 * | 6/2018 | Overmyer ........ A61B 17/07207 |
| 2018/0168745 A1 * | 6/2018 | Overmyer ........ A61B 17/07207 |
| 2018/0168751 A1 * | 6/2018 | Yi ........................ A61M 25/01 |

OTHER PUBLICATIONS

Lee Kyung-Min et al: "Shaft position measurement using dual absolute encoders", Sensors and Actuators A: Physical, Elsevier BV, NL, vol. 238, Dec. 30, 2015, pp. 276-281, XP029399652, ISSN: 0924-4247, DOI: 10.1016/J.SNA.2015.12.027.

\* cited by examiner

ROBOTIC SURGICAL TOOL, SYSTEM, AND METHOD

FIELD

Methods and devices are provided for measuring a rotational position of an elongate shaft on a surgical tool relative to an initial position.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

Various surgical tools and methods are provided for measuring a rotational position of an elongate shaft of a surgical tool.

In one embodiment, a robotic surgical tool is provided and includes a housing configured to couple to a plurality of motors on a tool driver of a surgical robot, and an elongate shaft that extends distally from the housing. The elongate shaft has an end effector coupled to a distal end thereof, and at least a portion of the elongate shaft is rotatable. The tool also has a belt that is coupled to the elongate shaft. The belt is configured to indicate a rotational position of the elongate shaft with respect to an initial rotational position of the elongate shaft.

In other embodiments, the belt can be configured to indicate a current rotational position of the shaft at positions of at least 360 degrees of rotation from the initial rotational position. The device can include numerous variations. For example, the device can have at least one sensor on the surgical tool for indicating the current rotational position of the elongate shaft. The device can also have a window in the housing that displays a portion of the belt. The belt can have a length that is greater than a circumference of the elongate shaft, which will allow measurement beyond 360 degrees of rotation. In other aspects, holes, printed lines, and/or magnetic stripes can be positioned along a length of the belt, and they can indicate the rotational position of the elongate shaft. An original indicator can be provided on the belt that is configured to indicate the original zero rotation position of the elongate shaft. In various embodiments, the belt can include a stop configured to prevent rotation of the elongate shaft beyond a preselected maximum rotational position. The surgical tool can also be configured so that it couples to a plurality of motors on a tool driver of a surgical robot such that rotation of the elongate shaft is driven by a motor.

In another embodiment, a surgical system is provided that has a surgical tool with an elongate shaft. The elongate shaft has an end effector at a distal end thereof, and the elongate shaft is rotatable about a longitudinal axis of the shaft. The surgical tool is configured to indicate an initial position in which the shaft has been rotated 0 degrees, and to measure a rotational position of the shaft from the initial position to a position beyond 360 degrees of rotation about the longitudinal axis.

There can be numerous variations to the system, though. For example, the system can include at least one sensor on the surgical tool that is configured to indicate the rotational position of the shaft. The system can also include a belt configured to engage the shaft to measure the rotational position of the shaft. Rotation of the shaft can cause corresponding rotation of the belt. The system can also include at least one roller that can be engaged between the belt and the shaft so that rotation of the shaft is transferred through the belt to cause rotation of the at least one roller. The belt can have a length greater than a circumference of the elongate shaft. The system can have a toothed gear on the shaft that is operably coupled to the belt. In some examples, the surgical tool can be configured so that it can couple to a plurality of motors on a tool driver of a surgical robot such that rotation of the shaft is driven by a motor.

In another aspect, a surgical method is provided that includes rotating a surgical tool about a longitudinal axis of an elongate shaft of the surgical tool, which rotates an end effector at a distal end of the surgical tool. The surgical tool also indicates a rotational position of the shaft beyond 360 degrees of rotation about the longitudinal axis relative to an initial rotational position.

In some embodiments, the method can also include coupling the surgical tool to a robotic surgical system. The surgical tool can communicate the rotational position to the robotic surgical system, and the method can also include a motor in the robotic surgical system that causes rotation of the shaft of the surgical tool.

BRIEF DESCRIPTION OF THE DRAWINGS

The invention will be more fully understood from the following detailed description taken in conjunction with the accompanying drawings, in which.

DETAILED DESCRIPTION

Figure 1:
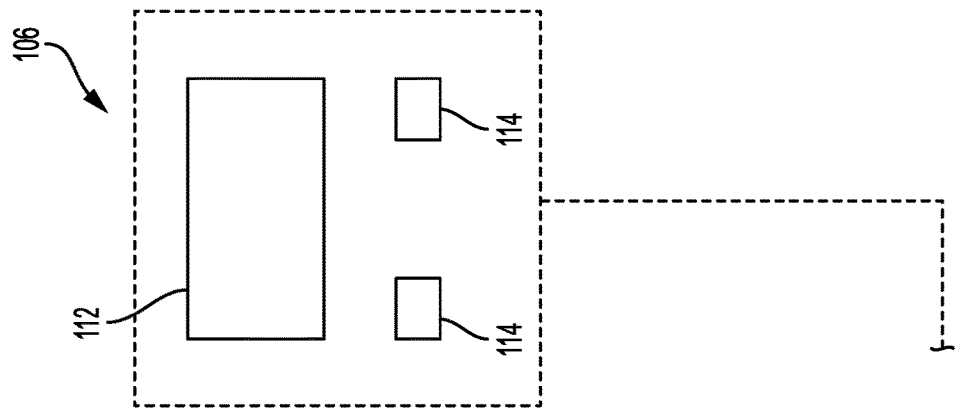
FIG. 1 is a perspective view of one embodiment of a surgical robotic system that includes a patient-side portion and a user-side portion.
Figure 1:
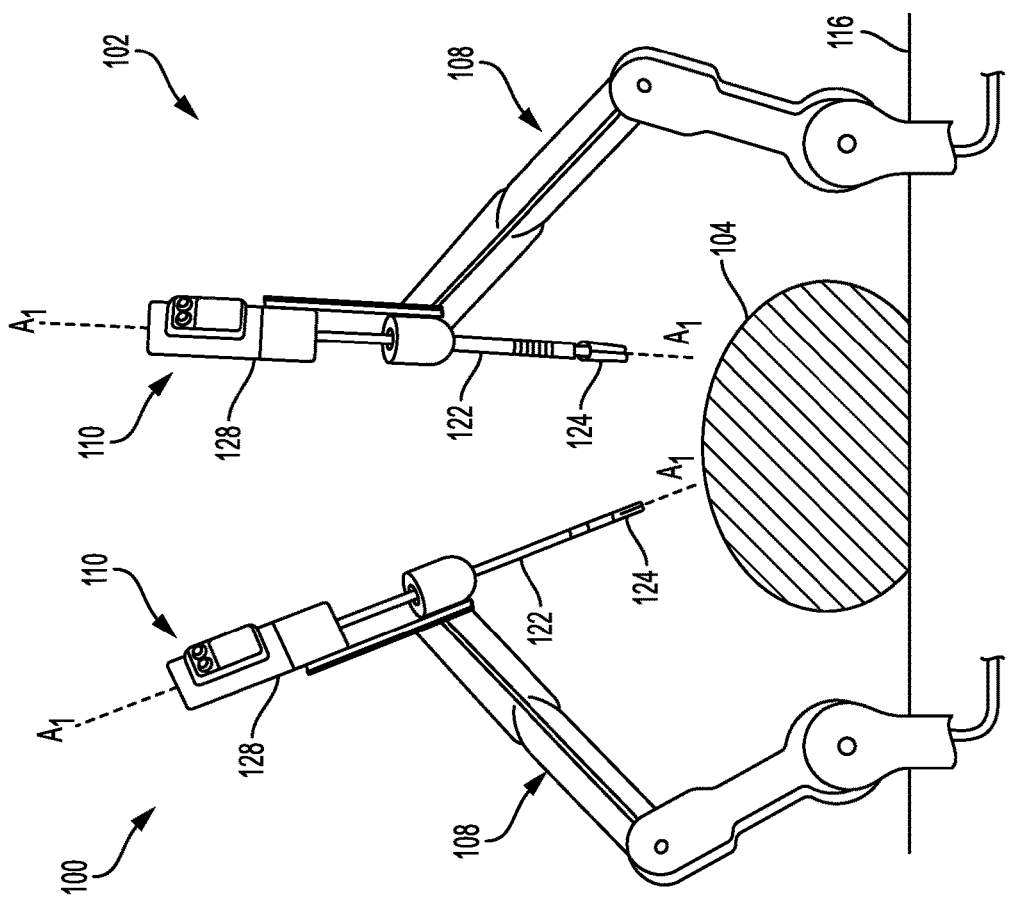
Figure 2:
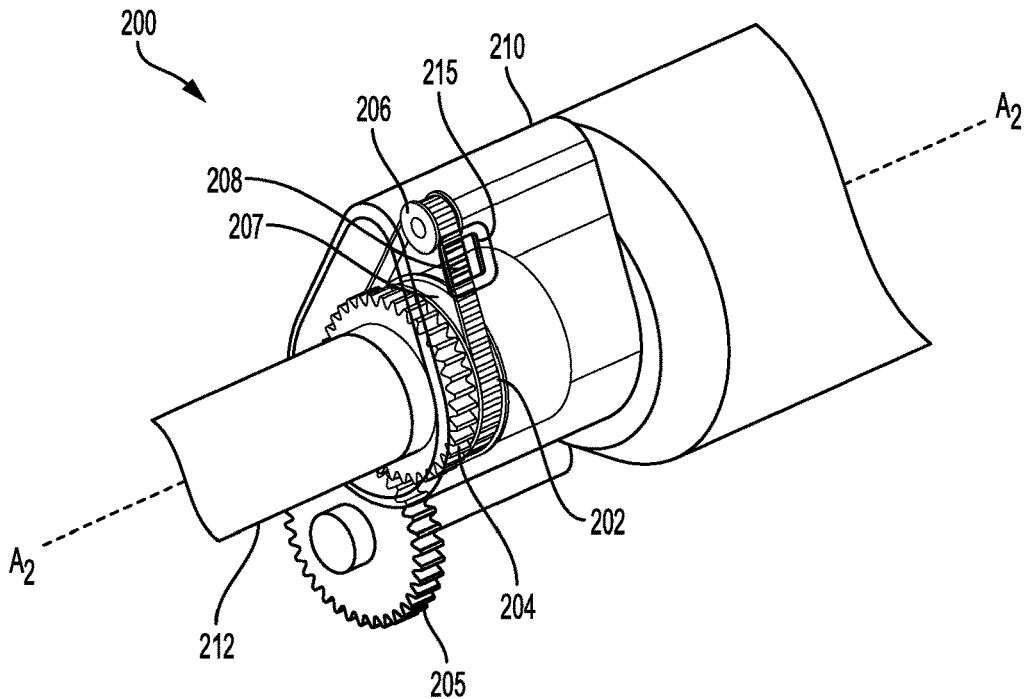
FIG. 2 is a perspective, partially-transparent view of a portion of a surgical tool.
Figure 3:
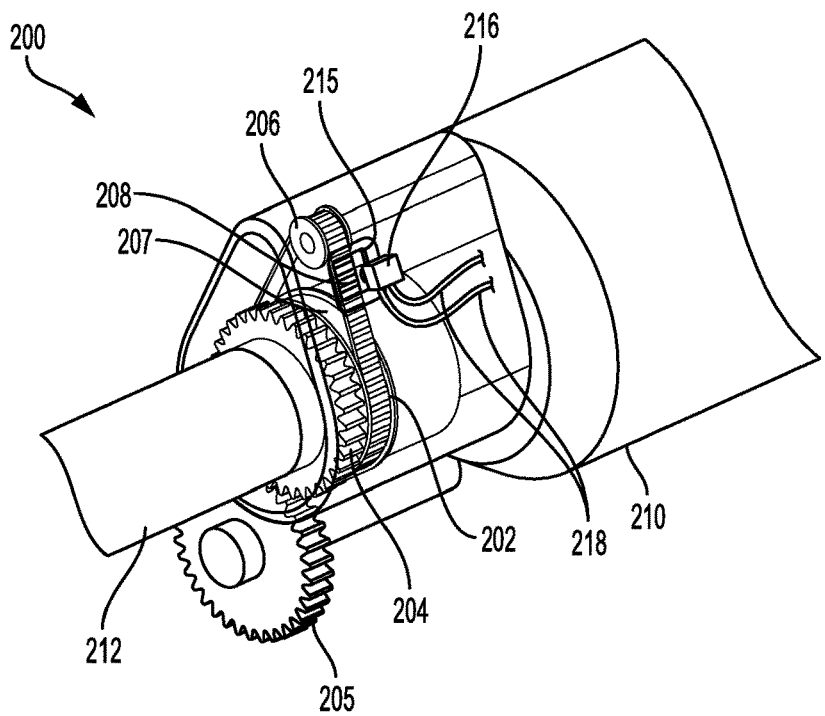
FIG. 3 is a perspective, partially-transparent view of the portion of the surgical tool of FIG. 2 with a sensor.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used. Additionally, WIPO Patent Publication No. WO2014/151621, filed on Mar. 13, 2014 and entitled "Hyperdexterous Surgical System," is incorporated herein by reference.

Various surgical tools and methods are provided in which a rotational position of an elongate shaft of a tool can be measured. Robotic surgical tools generally have a housing and an elongate tool shaft extending from the housing with an end effector on a distal end thereof. The housing has a plurality of actuators for causing various functions of the end effector, such as rotation, articulation, clamping, firing, stapling, etc. Many surgical tools with elongate shafts allow rotation of the shaft to provide a variety of benefits, such as more exact control and orientation of an end effector disposed on a distal end thereof. Because the housing attaches to a tool driver on a robotic arm that electromechanically drives the actuators to control the end effector, it is important for the robotic control system to know the rotational position of the shaft, and to know when the shaft is at the initial "zeroed" position.

This is important because the robotic control system will need to coordinate motion between shaft rotation and articulation of an end effector in order to resolve input commands, i.e., instructions, that are input into the system by the user. By way of example, if a shaft is rotated 180 degrees from an initial zero position, input commands instructing the end effector to articulate "left" from the user's viewpoint will need to be converted into instructions that cause the end effector to articulate "right" relative to the zero position of the shaft. By providing an indicator on the tool that indicates the rotational position of the shaft relative to the zero position, the system can modify user input instructions to account for the degree of shaft rotation. Knowing the rotational position of the shaft can also be important when a tool has rotational limits that exceed 360 degrees. By way of example, if a tool has a mechanical stop that limits rotation to 400 degrees from the zero position, markings on the shaft would not indicate that the shaft rotated beyond 360 degrees. Instead, any markings would only indicate that the shaft is 40 degrees from the zero position. Any attempt by the system to rotate the shaft beyond 40 degrees would cause the shaft to encounter the mechanical stop. Accordingly, the tools disclosed herein can be configured to indicate the rotational position beyond 360 degrees, thus allowing accurate control by the system. The ability to indicate the rotational position of a shaft can also be beneficial where a tool is detached and reattached from the tool driver on a surgical robot. In particular, the system can rotate the shaft to the initial zero angle position upon attachment, thus accounting for any unintended rotation that may have occurred while the tool was disconnected. Accordingly, various rotational angle measurement mechanisms are provided herein for measuring a rotational position of the shaft about a longitudinal axis through and preferably beyond 360 degrees of rotation.

FIG. 1 is a perspective iew of one embodiment of a surgical robotic system 100 that includes a patient-side portion 102 that is positioned adjacent to a patient 104, and a user-side portion 106 that is located a distance from the patient, either in the same room and/or in a remote location. The patient-side portion 102 generally includes one or more robotic arms 108 and one or more surgical tools and/or tool assemblies 110 that are configured to releasably couple to a robotic arm 108. The user-side portion 106 generally includes a vision system 112 for viewing the patient 104 and/or surgical site, and a control system 114 for controlling the movement of the robotic arms 108 and each surgical tool 110 during a surgical procedure.

The surgical tool 110 includes an elongate shaft 122, an end effector 124, and a tool housing 128 coupled to a proximal end of the shaft 122. The shaft 122 can have any of a variety of configurations. In general, the shaft 122 is an elongate member extending distally from the housing 128 and having at least one inner lumen extending therethrough. The shaft 122 is fixed to the housing 128, but in other embodiment the shaft 122 can be releasably coupled to the housing 128 such that the shaft 122 can be interchangeable with other shafts. This may allow a single housing 128 to be adaptable to various shafts having different end effectors. The end effector 124 can also have a variety of sizes, shapes, and configurations. The end effector 124 can be configured to move relative to the shaft 122, e.g., by rotating and/or articulating, to position the end effector 124 at a desired location relative to a surgical site during use of the tool 110. The housing 128 includes various components (e.g., gears and/or actuators) configured to control the operation various features associated with the end effector 124 (e.g., any one or more of clamping, firing, rotation, articulation, energy delivery, etc.). The shaft 122, and hence the end effector 124 coupled thereto, can be configured to rotate about a longitudinal axis A1 of the shaft 122, and components within the housing 128 can be configured to control the rotational movement of the shaft 122. In at least some embodiments, as in this illustrated embodiment, the surgical tool 110 is configured to releasably couple to the robotic arm 108, and the tool housing 128 can include coupling features configured to allow the releasable coupling of the tool 110 to the robotic arm 108. A person skilled in the art will appreciate that the surgical tool 110 can have any of a variety of configurations, and it can be configured to perform at least one surgical function. The surgical tool can be, for example, a stapler, a clip applier, forceps, a grasper, a needle driver, scissors, an electrocautery tool that applies energy, a suction tool, an irrigation tool, an imaging device (e.g., an endoscope or ultrasonic probe), etc.

The control system 114 can have a variety of configurations and can be located adjacent to the patient (e.g., in the operating room), remote from the patient (e.g., in a separate control room), or distributed at two or more locations (e.g., the operating) and/or separate control room(s)). As an example of a distributed system, a dedicated system control console can be located in the operating room, and a separate console can be located in a remote location. The control system 114 can include components that enable a user to view a surgical site of the patient 104 being operated on by the patient-side portion 102 and/or to control one or more parts of the patient-side portion 102 (perform a surgical procedure at the surgical site). In some embodiments, the control system 114 can also include one or more manually-operated input devices, such as a joystick, exoskeletal glove, a powered and gravity-compensated manipulator, or the like. The one or more input devices can control teleoperated motors which, him turn, control the movement of the surgical system, including the robotic arms 108 and surgical tools 110.

The patient-side portion 102 can have a variety of configurations. As illustrated in FIG. 1, the patient-side portion 102 can couple to an operating table 116. However, in other embodiments, the patient-side portion 102 can be mounted to a wall, to the ceiling, to the floor, or to other operating room equipment. Further, while the patient-side portion 102 is shown as including two robotic arms 108, more or fewer robotic arms 108 may be included. Furthermore, the patient-side portion 102 can include separate robotic arms 108 mounted in various positions, such as relative to the surgical table 116 (as shown in FIG. 1). Alternatively, the patient-side portion 102 can include a single assembly that includes one or more robotic arms 108 extending therefrom.

As indicated above, in an exemplary embodiment a surgical tool is provided having an indicator for indicating a rotational position of a shaft of the tool relative to a zero or initial position. The term "shaft" as used herein is intended to include the entire shaft or any portion of the shaft, including the end effector mounted on the distal end thereof. The term "rotational position" is intended to refer to the exact position of a point on the shaft relative to an initial or zero position of the point on the shaft. The "rotational position" can be determined by measuring the degrees of rotation of the point on the shaft from an initial, zero degree position of the point on the shaft. In certain aspects, the "rotational position" can be measured through and beyond 360 degrees of rotation from the initial, zero degree position.

A variety of different mechanisms can be used to measure a rotational position of a shaft of a surgical tool, and to communicate that position to a robotic system. FIGS. 2-5 illustrate one embodiment of a tool 200 having a housing 210 and a shaft 212 extending distally therefrom. The tool housing 210 includes a belt 202, such as a timing belt, for measuring the rotational position of the shaft 212 of the tool 200. The belt 202 is positioned within the housing 210 and extends circumferentially around the shaft 212. Rotation of the shaft 212 causes corresponding rotation of the belt 202, and thus the belt 202 can be used to indicate the rotational position of the shaft 212. Rotation of the shaft 212 can be driven using various techniques, but in the illustrated embodiment the shaft includes a toothed gear 204 formed thereon that is configured to be driven by a gear assembly 205, which in turn can be driven by a motor in a tool driver on a surgical robot. The gear 204 can have a circular receiving channel 207 that can be configured to receive the belt 202 therein such that the belt 202 rotates with rotation of the gear 204.

Figure 4:
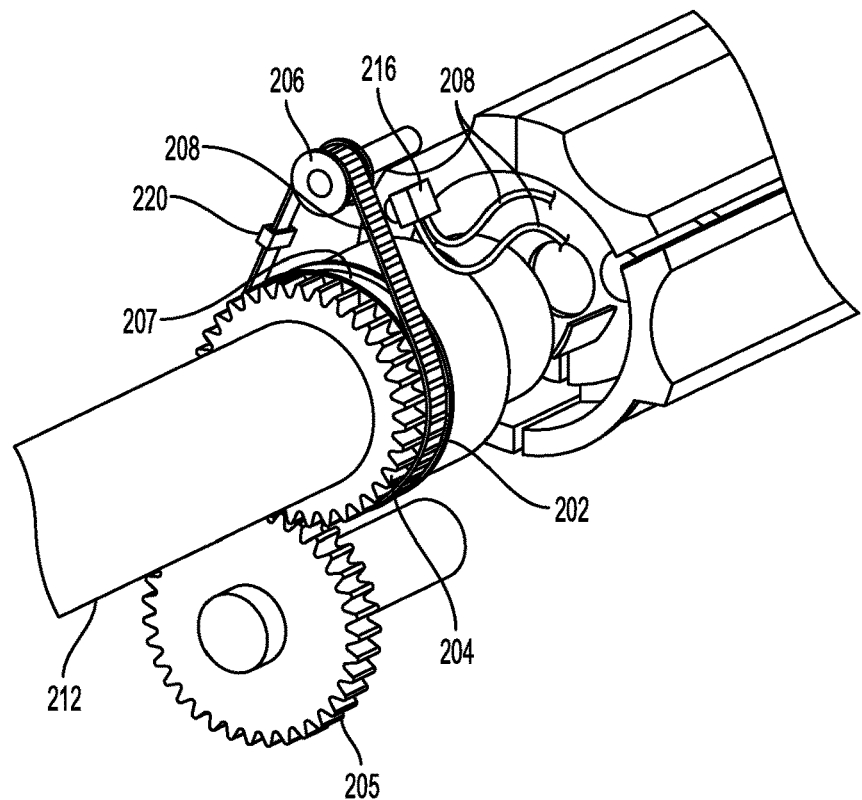
FIG. 4 is a perspective view of the portion of the surgical tool of FIG. 3 with a housing.
Figure 5:
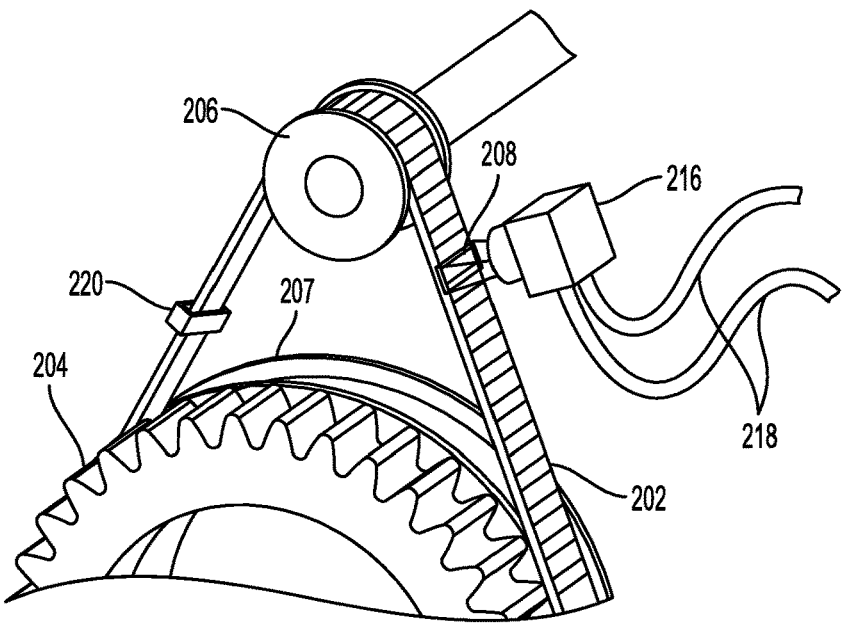
FIG. 5 is a perspective view of the portion of the surgical tool of FIG. 3 with a housing removed.

In an exemplary embodiment, a total length of the belt 202 can be configured to be greater than a circumference of the shaft 212 to allow the belt 202 to measure and communicate a rotational position of the shaft up to and greater than 360 degrees. By providing a belt having a circumference that exceeds the shaft, the belt 202 can measure 360 degrees of rotation of the shaft, plus an additional amount of rotation as dictated by any additional length of the belt 202 as compared to the circumference of the shaft 212. By way of example, the belt 202 can have a length that allows for measurement of rotation of the shaft 212 through 380 degrees in each direction, for a total rotation of 760 degrees. The circumference of the shaft (e.g., 1.57 inches) can be multiplied by the ratio of the total rotation to 360 (e.g., 760/360=2.11) to obtain a total belt length (e.g., 3.31 inches). A person skilled in the art will appreciate that the belt length can be selected based on the desired amount of rotation to be measured. Where a belt having a specified length is desired to measure rotation of the shaft up to a certain position, e.g., beyond 360 degrees, a stop can optionally be provided to prevent rotation of the belt 202 when the shaft 212 has reached its maximum rotational position. For example, a stop 220 is illustrated in FIGS. 4-5. In some embodiments, the stop can be a mechanical stop, such as a tab or protrusion that prevents additional rotation of the belt 202. In other embodiments, the stop can be a marking, sensor, or other feature that allows the system to detect when the shaft has reached it maximum rotational position.

In order to accommodate the excess length of the belt 202 as compared to the shaft 212, while still providing simultaneous rotation, a roller 206 can be disposed in contact with the belt 202. The roller 206 can be axially displaced from a longitudinal axis A2 of the shaft 212, such that it is not mechanically coupled to the shaft. While not shown, it can be mounted in a fixed rotational position within the housing. In use, rotation of the shaft 212 can be configured to cause simultaneous rotation of the belt 202, which in turn can be configured to cause rotation of the roller 206.

Various techniques can be used to measure or indicate the rotational position of the shaft. In one embodiment, a plurality of detection markings 208 can be formed on the belt 202 and can be visible through a window or opening 215 in the housing 210. The detection markings 208 can extend along a length of the belt 202 and can represent a known pattern to allow the robotic control system to identify the position of each marking, and thereby determine the rotational position of the shaft 212. For example, each marking can differ in width or length relative to one another. One of the markings is preferably located at an initial, zero position to indicate the initial, unrotated position of the shaft. As the shaft 212 rotates, the belt 202 is configured to rotate with the shaft 212, thereby causing the detection markings 208 to move relative to the opening 215. Because the zero rotation position of the shaft 212 is known and because the pattern of the detection markings 208 is known, the current rotational position of the shaft 212 can be determined by detecting the particular detection marking 208 visible within the opening 215 in the housing 210.

A person skilled in the art will appreciate that the markings 208 can have any configuration, but are preferably visible (via visible light or infrared light) to the system. In other embodiments, magnets can be used to indicate the rotational position of the shaft. The markings also need not extend around the entire circumference of the belt. For example, there can be markings on the belt just at the initial or zero position of the shaft, there can be markings just at the end or terminal positions of the belt, or anywhere in between. The detection markings can take a variety of forms, such as holes, printed lines, magnetics stripes, letters, shapes, etc.

The robotic system can include a sensor system that can detect the markings 208 and identify the rotational position of the shaft 212. For example, a sensor 216 can be disposed outside of the housing 210 and arranged to detect the markings 208 through the opening 215. The sensor 216 can be coupled to the robotic system through wires 218. In other embodiments, the sensor can be wireless. While sensor 216 is disposed outside of the housing 210, sensors can be disposed within the housing or incorporated into the housing. In such embodiments, the window or cutout can optionally be eliminated. Because markings will be detectable through and beyond 360 degrees of rotation of the shaft 212, due to the excess belt length, the system can detect the rotational position of the shaft beyond 360 degrees of rotation. Moreover, because the system is able to detect and identify the zero rotation position, the system can use the markings to identify the direction of rotation as well. In some embodiments, the sensor can be configured to detect the markings through the housing such that a window or cutout is not required even when the sensor is disposed outside of the housing. A control system, such as the control system 114, can be in communication with and can help the sensor system to detect the detection marking and report a rotational position of a shaft to an overall surgical system, such as a robotic surgical system.

In use, the tool 200 can be part of a robotic system and controlled by a control system, such as the control system 114, to maneuver to and around a surgical site. As the tool 200 is positioned for use, the shaft 212 can be rotated to orient an end effector disposed on a distal end thereof and controllable by the tool 200. As the shaft 212 rotates, the gear 204 with the receiving channel 207 will also rotate. Rotation of the receiving channel 207 will cause the belt 202 to move, allowing the markings 208 to pass by the opening 215 and the sensor 216. The sensor 216 can detect the markings 208 through the opening 215 and report information to the robotic system regarding rotation of the shaft 212, such as the rotational position.

Figure 6:
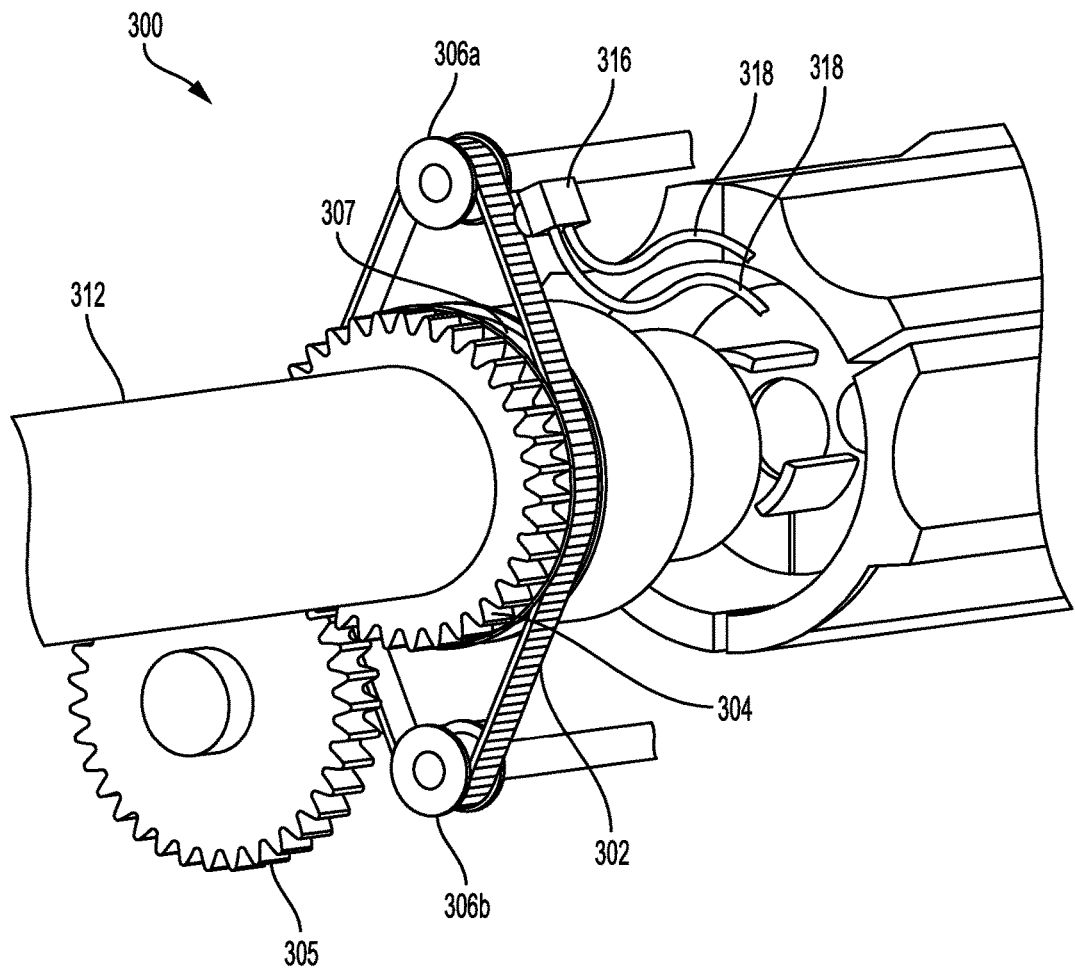
FIG. 6 is a perspective view of another embodiment of a surgical tool.

FIG. 6 illustrates another embodiment of a tool 300 in which two rollers 306a, 306b are provided for accommodating a larger belt 302. In this embodiment, the tool 300 can have a housing (not shown) and a shaft 312 extending distally therefrom. The belt 302 can be disposed within the housing and can be configured to measure the rotational position of the shaft 312. The belt 302 can extend circumferentially around the shaft 312. Rotation of the shaft 312 can be configured to cause corresponding rotation of the belt 302, and thus the belt 302 can be configured to indicate the rotational position of the shaft 312. Rotation of the shaft 312 can be configured to be driven using various techniques, but in the illustrated embodiment the shaft includes a toothed gear 304 formed thereon that is configured to be driven by a gear assembly 305 with a motor in a tool driver on a surgical robot. The gear 304 can have a circular receiving channel 307 that can be configured to receive the belt 302 therein and rotate with rotation of the gear 304.

In an exemplary embodiment, a total length of the belt 302 can be configured to be greater than a circumference of the shaft 312 to allow the belt 302 to measure and communicate a rotational position of the shaft up to and greater than 360 degrees. The total length of the belt 302 is significantly larger than the circumference of the shaft 312 in this embodiment because an additional length of the belt 302 can be received on the two rollers 306a, 306b, thus allowing the rotational position of the shaft 312 to be measured up to a higher degree, e.g., 400 degrees in each direction. As shown in FIG. 6, the first roller 306a is positioned on one side of the shaft 312, and the second roller 306b is positioned on an opposite side of the shaft 312. However, the position of the two rollers 306a, 306b can vary. Moreover, any number of rollers can be provided as may be needed based on the desired maximum rotational position that the belt is configured to indicate. As with the embodiment of FIG. 2, the rollers 306a, 306b are configured to rotate in coordination with rotation of the belt, thus allowing the larger belt 302 to rotate simultaneously with the shaft 312. As discussed above regarding the belt 202, a stop can optionally be provided to prevent rotation of the belt 302 when the shaft 312 has reached its maximum rotational position.

A plurality of detection markings 308 can be formed on the belt 302 and can be visible through a window or opening (not shown) in the housing. The detection markings 308 can extend along a length of the belt 302 and can represent a known pattern to allow the robotic control system to identify the position of each marking, and thereby determine the rotational position of the shaft 312. For example, each marking can differ in width or length relative to one another. One of the markings 308 is preferably located at an initial, zero position to indicate the initial, unrotated position of the shaft. As the shaft 312 rotates, the belt 202 can be configured to rotate with the shaft 312, thereby causing the detection markings 308 to move relative to the window. Because the zero rotation position of the shaft 312 is known and because the pattern of the detection markings 308 is known, the current rotational position of the shaft 312 can be determined by detecting the particular detection marking 308 detectable within the window in the housing. Any configuration can be used for the markings 308, similar to markings 208.

The robotic system can include a sensor system that can detect the markings 308 and identify the rotational position of the shaft 312. For example, a sensor 316 can be disposed outside of the housing and arranged to detect the markings 308. The sensor 316 can be coupled to the robotic system through wires 318. In other embodiments, the sensor can be wireless. While sensor 316 is disposed outside of the housing, sensors in other embodiments can be disposed within the housing or incorporated into the housing. In such embodiments, the window or cutout can optionally be eliminated.

In use, the tool 300 can be part of a robotic system and controlled by a control system, such as the control system 114, to maneuver to and around a surgical site. As the tool 300 is positioned for use, the shaft 312 can be rotated to orient an end effector disposed on a distal end thereof and controllable by the tool 300. As the shaft 312 rotates, the gear 304 with the receiving channel 307 will also rotate. Rotation of the receiving channel 307 will cause the belt 302 to move, allowing the markings 308 to pass by the window and the sensor 316. The sensor 316 can detect the markings 308 through the window and report information to the robotic system regarding rotation of the shaft 312, such as a rotational position.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

The systems, devices, and methods disclosed herein can be implemented using one or more computer systems, which may also be referred to herein as digital data processing systems and programmable systems.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A robotic surgical tool, comprising:
a housing configured to couple to a surgical robot;
an elongate shaft extending distally from the housing and having an end effector coupled to a distal end thereof, at least a portion of the elongate shaft being rotatable; and
a belt coupled to the elongate shaft, the belt being configured to indicate a rotational position of the elongate shaft with respect to an initial rotational position of the elongate shaft, the belt including a stop protrusion surrounding an outer perimeter of the belt and configured to prevent rotation of the elongate shaft beyond a preselected maximum rotation position.

2. The surgical tool of claim 1, wherein the belt indicates a current rotational position of the shaft at positions of at least 360 degrees of rotation from the initial rotational position.

3. The surgical tool of claim 1, further comprising at least one sensor on the surgical tool for detecting a current rotational position of the elongate shaft.

4. The surgical tool of claim 1, further comprising a window in the housing configured to reveal a portion of the belt therethrough.

5. The surgical tool of claim 1, wherein the belt has a length greater than a circumference of the elongate shaft.

6. The surgical tool of claim 1, wherein at least one of holes, printed lines, and magnetic stripes are positioned along a length of the belt for indicating the rotational position of the elongate shaft.

7. The surgical tool of claim 1, further comprising a first indicator on the belt configured to indicate the initial rotational position of the elongate shaft.

8. The surgical tool of claim 1, wherein rotation of the elongate shaft is configured to be driven by the surgical robot.

9. The surgical tool of claim 1, wherein the shaft includes a gear formed thereon that is configured to be driven by a gear assembly.

10. The surgical tool of claim 9, wherein the gear has a circular receiving channel configured to receive the belt therein such that the belt rotates with rotation of the gear.

11. A surgical system, comprising:
a surgical tool including an elongate shaft having an end effector at a distal end thereof, the elongate shaft being rotatable about a longitudinal axis of the shaft, the surgical tool having a belt configured to indicate an initial position in which the shaft has been rotated 0 degrees and to indicate a rotational position of the shaft from the initial position to a position beyond 360 degrees of rotation about the longitudinal axis wherein a toothed gear is positioned on the shaft and is operably coupled to the belt.

12. The system of claim 11, further comprising at least one sensor on the surgical tool for indicating the rotational position of the shaft.

13. The system of claim 11, wherein rotation of the shaft causes corresponding rotation of the belt.

14. The system of claim 11, further comprising at least one roller engaged between the belt and the shaft such that rotation of the shaft is transferred through the belt to cause rotation of the at least one roller.

15. The system of claim 11, wherein the belt has a length greater than a circumference of the elongate shaft.

16. The system of claim 11, wherein the surgical tool is configured to couple to a surgical robot such that rotation of the shaft is driven by the surgical robot.

17. A surgical method, comprising:
   rotating a surgical tool about a longitudinal axis of an elongate shaft of the surgical tool to thereby rotate an end effector at a distal end of the surgical tool, the surgical tool having a belt and a sensor adjacent to the belt, rotation of the surgical tool causing corresponding rotation of the belt, and the sensor monitoring a plurality of indicators on the belt for indicating a rotational position of the shaft beyond 360 degrees of rotation about the longitudinal axis relative to an initial rotational position.

18. The method of claim 17, further comprising coupling the surgical tool to a robotic surgical system, the surgical tool communicating the rotational position to the robotic surgical system.

19. The method of claim 18, wherein the robotic surgical system causes rotation of the shaft of the surgical tool.

20. The method of claim 17, wherein the sensor monitors the plurality of indicators including at least one of holes, printed lines, and magnetic stripes positioned along an outward facing surface of the belt.

* * * * *